United States Patent
Murota et al.

(10) Patent No.: US 8,569,261 B2
(45) Date of Patent: Oct. 29, 2013

(54) VASCULAR PROTECTING AGENT HAVING SALT-ABSORPTION INHIBITORY ACTIVITY

(75) Inventors: Itsuki Murota, Ibaraki (JP); Yoshio Uehara, Tokyo (JP)

(73) Assignee: Maruha Nichiro Foods, Inc., Tokyo (JP)

(*) Notice: Subject to any disclaimer, the term of this patent is extended or adjusted under 35 U.S.C. 154(b) by 9 days.

(21) Appl. No.: 13/219,969

(22) Filed: Aug. 29, 2011

(65) Prior Publication Data

US 2012/0058967 A1 Mar. 8, 2012

(30) Foreign Application Priority Data

Aug. 31, 2010 (JP) .................................. 2010-193756
Aug. 10, 2011 (JP) .................................. 2011-174853

(51) Int. Cl.
*A61K 31/715* (2006.01)

(52) U.S. Cl.
USPC .......................................................... 514/54

(58) Field of Classification Search
USPC .......................................................... 514/54
See application file for complete search history.

(56) References Cited

U.S. PATENT DOCUMENTS

| | | | |
|---|---|---|---|
| 5,460,957 A | 10/1995 | Hiura et al. | |
| 5,516,666 A | 5/1996 | Nozomi et al. | |
| 2010/0080788 A1* | 4/2010 | Barnett et al. ............... | 424/94.5 |
| 2010/0256090 A1 | 10/2010 | Yu et al. | |

FOREIGN PATENT DOCUMENTS

| | | | |
|---|---|---|---|
| JP | 5-304974 A | 11/1993 | |
| JP | 6-237783 A | 8/1994 | |
| JP | 11-43439 A | 2/1999 | |
| JP | 2002-272420 | 9/2002 | |
| JP | 2005-145885 A | 6/2005 | |
| WO | WO 2005/026344 A1 | 3/2005 | |
| WO | WO 2009/086685 A1 | 7/2009 | |

OTHER PUBLICATIONS

Extended European Search Report issued Mar. 21, 2012, in Patent Application No. 11179548.0.

Takamitsu Chaki, et al., "Metabolism and Calcium Antagonism of Sodium Alginate Oligosaccharides", Bioscience Biotechnology and Biochemistry, vol. 71, No. 8, XP 2670436, Aug. 2007, pp. 1819-1825.

Takamitsu Chaki, et al., "Dose Dependency of Sodium Alginate Oligosaccharides in a Randomized Double-blind Placebo-controlled Clinical Study in Subjects with High Normal Blood Pressure and Mild Hypertension", Japanese Pharmacology and Therapeutics, vol. 34, No. 11, XP 9156902, (2006), pp. 1267-1277.

Takamitsu Chaki, et al., "Hypotensive Response and Safety of Long Term Sodium Alginate Oligosaccharides Intake in Subjects with High Normal Blood Pressure and Mild Hypertension", Japanese Pharmacology and Therapeutics, vol. 35, No. 5, XP 9156903, (2007), pp. 519-531 (with English Abstract and English translation).

Toru Nishikawa, et al., "Detection and Pharmacokinetics of Alginate Oligosaccharides in Mouse Plasma and Urine after Oral Administration by a Liquid Chromatography/Tandem Mass Spectrometry (LC-MS/MS) Method", Bioscience Biotechnology and Biochemistry, vol. 72, No. 8, XP 2670437, Aug. 2008, pp. 2184-2190.

Office Action issued Dec. 18, 2012 in Japanese Patent Application No. 2011-174853.

A. Mirshafiey et al., Production of M2000 (β-D-mannuronic acid) and its therapeutic effect on Experimental nephritis, Environmental toxicology and Pharmacology, vol. 24, No. 1, 2007, pp. 60-66 with cover page.

Office Action issued Mar. 12, 2013, in Japanese Patent Application No. 2011-174853.

Masahiro Katoh, "Patho-morphological Study of Progression and Sclerotic Change of Glomerular Lesions in Serum Sickness Nephritis in Rats", Shinshu Med. J., vol. 34, No. 1, 1986, pp. 56-74 (with English translation).

Keizo Komoda, "Immunopathological study of chronic serum sickness after the onset thereof in rats", Journal of Okayama Medical Association, vol. 102, 1990, pp. 819-830 (with English translation).

* cited by examiner

*Primary Examiner* — Wu-Cheng Winston Shen
*Assistant Examiner* — Yih-Horng Shiao
(74) *Attorney, Agent, or Firm* — Oblon, Spivak, McClelland, Maier & Neustadt, L.L.P.

(57) ABSTRACT

This invention provides a vascular protecting agent having salt-absorption inhibitory activity with the use of alginate oligosaccharide salt absorbed by the body via degradation to an oligosaccharide, so that a patient can easily and safely ingest such agent on a routine basis. A vascular protecting agent having salt-absorption inhibitory activity comprises, as an active ingredient, alginate oligosaccharide obtained by treating sodium alginate with a *Pseudoalteromonas* microorganism or a processed product thereof and/or a salt thereof.

12 Claims, 11 Drawing Sheets n = 8, mean ± standard deviation, a, b, c, d; Bonferroni/Dunn (p = 0.05, significant difference is observed between different symbols)

n = 8, mean ± standard deviation, a, b, c; Bonferroni/Dunn (p = 0.05, significant difference is observed between different symbols)

n = 8, mean ± standard deviation, a, b, c; Bonferroni/Dunn (p = 0.05, significant difference is observed between different symbols)

n = 8, mean ± standard deviation, a, b, c; Bonferroni/Dunn (p = 0.05, significant difference is observed between different symbols)

n = 8, mean ± standard deviation, a, b, c; Steel-Dwass (p = 0.05, significant difference is observed between different symbols)*; Steel (vs Control group, p = 0.05)

n = 8, mean ± standard deviation, a, b, c; Bonferroni/Dunn (p = 0.05, significant difference is observed between different symbols)

n = 8, mean ± standard deviation, a, b, c; Bonferroni/Dunn (p = 0.05, significant difference is observed between different symbols)

n =6 or 7, mean ± standard deviation, Bonferroni/Dunn (p = 0.05, significant difference is observed between different symbols)

VASCULAR PROTECTING AGENT HAVING SALT-ABSORPTION INHIBITORY ACTIVITY

CROSS-REFERENCE TO RELATED APPLICATIONS

The present application claims priority to Japanese patent applications JP 2011-174853, filed on Aug. 10, 2011 and JP 2010-193756, filed on Aug. 31, 2010.

TECHNICAL FIELD

The present invention relates to a vascular protecting agent having salt-absorption inhibitory activity.

BACKGROUND ART

Many diseases associated with vascular disorders have few subjective symptoms. Organ dysfunctions are occasionally caused as symptoms become serious while patients are unaware thereof. In the case of heart disease, for example, such symptoms could directly lead to death. An example of an organ in which many blood vessels are present is the kidney. A blood vessel that has entered into the kidney branches into capillary blood vessels, and the resulting capillary blood vessels are coiled to form tissue referred to as a "glomerulus" having a spherical form. Metabolic products, extraneous materials, and the like that are not necessary for living organisms are filtered through the glomeruli and excreted into the urine in the end. The amount of blood transferred to the kidney is as much as approximately 200 ml every minute, and the amount of primitive urine filtered is said to be as much as 120 liters every day. The condition in which the blood vessels forming the glomeruli are damaged by various factors and 60% or more normal kidney functions are lost is referred to as kidney failure. When the remaining functions are 15% or more below the normal level, continuous dialysis treatment becomes necessary. Dialysis treatment requires a patient to visit a medical facility providing such treatment about 3 times a week, and each instance of dialysis treatment is provided by a specialist stuff over a period of 4 to 5 hours. Receiving dialysis treatment is equivalent to machine-dependent life maintenance, and it imposes serious economical hardship upon patients, in addition to significant lifestyle changes. Accordingly, delay of the initiation of dialysis is significant. It is said that as many as 250,000 patients receive dialysis treatment in Japan.

Japanese people have been familiar with high-salt foods, such as salt, soy sauce, and soybean paste, since ancient times. When excess salt intake surpasses the capacity of the kidney for salt elimination, the salt concentration in the body is elevated. As a result, the water content in the body is increased in order to reduce the salt concentration of the body fluid, which increases the vascular resistance, and sodium in salt stimulates the sympathetic nervous system or cell membrane to contract blood vessels. This imposes excessive burdens on blood vessels. If chronic stress imposed on blood vessels exhausts the heart or kidney and the organ becomes dysfunctional, organ transplantation or dialysis treatment becomes necessary when symptoms are serious. While a low-sodium diet is effective, low-salt foods are unbearable for Japanese people, who have been accustomed to salt since ancient times. In particular, elderly people with decreased taste sensitivity for salt may unfavorably continue to ingest excessive salt unawarely. Accordingly, many studies have heretofore been made regarding elimination of salt from the body, such as elimination from the body with the aid of Na—K exchange action utilizing dietary fiber.

In contrast, alginic acid is a polysaccharide with high viscosity contained in brown algae, such as *Laminaria*. Low-molecular-weight alginic acid resulting from degradation of alginate polysaccharide via heating under acidic conditions to result in a molecular weight of several tens of thousands to several hundreds of thousands is prepared in the form of sodium or potassium salt, and the resultant is used as a food additive in the form of a thickener. In general, it is considered that alginic acid is not absorbed by the intestinal tract, and it is reported that low-molecular-weight alginate is not absorbed by the small intestine and is not substantially digested by enteric bacteria in the large intestine (New Food Industry, 43, 2, 13-19, 2001). Salt of alginate polysaccharide or low-molecular weight alginic acid (e.g., potassium or calcium salt) is known to cause exchange of sodium ions and excretion of sodium ions from the body without absorption by the intestinal tract.

In addition, salt of alginate polysaccharide or that of low-molecular-weight alginate is treated with a *Pseudoalteromonas* microorganism or a processed product thereof to degrade such salt into an oligosaccharide. Patent applications have been filed for food products with high water solubility, low viscosity, and absorbability in the body that inhibit blood pressure elevation with the use of a salt of alginate oligosaccharide (JP Patent Publication (Kokai) No. 2002-272420 A), vascular endothelial growth accelerators (JP Patent Publication (Kokai) No. H11-43439 A (1999)), and preventive and therapeutic agents for circulatory diseases (JP Patent Publication (Kokai) No. H09-235234 A (1997)).

SUMMARY OF THE INVENTION

Object to be Attained by the Invention

An object of the present invention is to provide a vascular protecting agent exhibiting salt-absorption inhibitory activity, which is characterized in that it comprises alginate oligosaccharide and/or a salt thereof.

Means for Attaining the Object

The present inventors have conducted concentrated studies in order to attain the above object. As a result, they discovered that alginate oligosaccharide and/or a salt thereof is absorbed by the body, unlike existing salt of alginate polysaccharide or that of low-molecular-weight alginate, and alginate oligosaccharide and salts thereof exhibit salt-absorption inhibitory activity through a mechanism different from that of existing salts of alginate polysaccharide or low-molecular-weight alginate, while existing salts of alginate polysaccharide or low-molecular-weight alginate absorb salt and the resultant is removed from the body, thus resulting in salt-absorption inhibitory activity. They also discovered that alginate oligosaccharide and/or a salt thereof would exhibit activity of protecting blood vessels.

Specifically, the present invention is as follows.

The present invention provides a vascular protecting agent comprising, as an active ingredient, alginate oligosaccharide and/or a salt thereof and having salt-absorption inhibitory activity.

In addition, the present invention provides a vascular protecting agent having salt-absorption inhibitory activity, wherein the alginate oligosaccharide and/or a salt thereof is obtained by treating sodium alginate with a *Pseudoalteromonas* microorganism or a processed product thereof.

Further, the present invention provides a vascular protecting agent having salt-absorption inhibitory activity, wherein the *Pseudoalteromonas* microorganism is the *Pseudoalteromonas* sp. strain No. 1786.

Further, the present invention provides a vascular protecting agent having salt: absorption inhibitory activity, wherein the alginate oligosaccharide and/or a salt thereof is represented by formula 1 below:

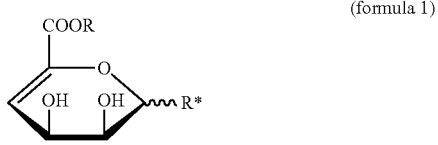

(formula 1)

in formula 1, R represents a hydrogen atom or metal ion; R' represents D-mannuronic acid (M) represented by formula 2 or L-guluronic acid (G) represented by formula 3; and two or more constitutive sugars comprising either or both M and G as constitutive sugars have an α- and/or β-1,4-bound structure:

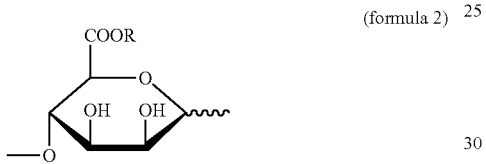

(formula 2)

in formula 2, R is as defined above; and

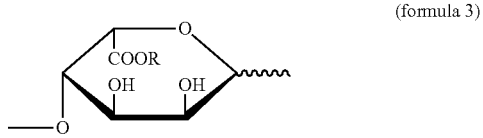

(formula 3)

in formula 3, R is as defined above.

Further, the present invention provides an agent for inhibiting deterioration of renal functions and an agent for inhibiting deterioration of cardiac functions comprising the vascular protecting agent.

Furthermore, the present invention provides the vascular protecting agent, the agent for inhibiting deterioration of renal functions, and the agent for inhibiting deterioration of cardiac functions in the form of subcutaneously-administered agents.

EFFECTS OF THE INVENTION

According to the present invention, adverse effects imposed by excessive salt stress can be reduced via ingestion of alginate oligosaccharide and/or a salt thereof, and a patient can easily and safely ingest alginate oligosaccharide and/or a salt thereof on a routine basis. Thus, the present invention is effective for health maintenance.

EMBODIMENTS FOR CARRYING OUT THE INVENTION

Figure 1:
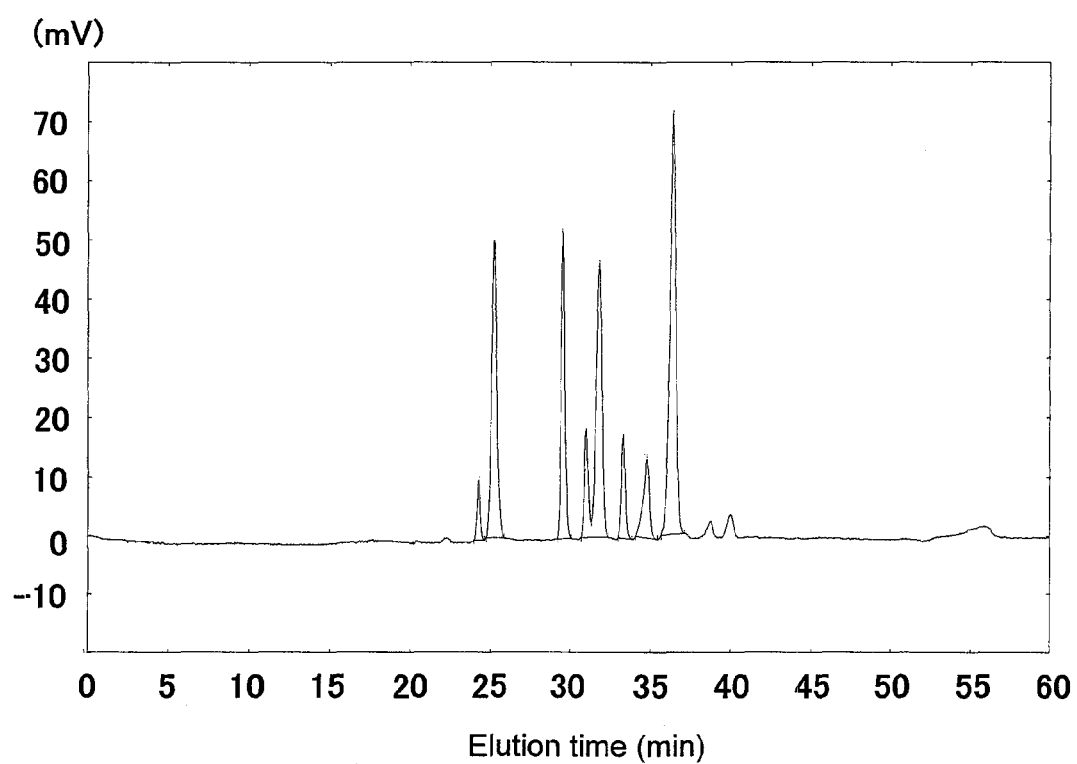
FIG. 1 shows the results of HPLC analysis of sodium alginate oligosaccharide obtained by treatment with alginate lyase derived from the lyophilized *Pseudoalteromonas* sp. strain No. 1786.

Hereafter, the present invention is described in detail.

The vascular protecting agent having salt-absorption inhibitory activity of the present invention comprises, as an active ingredient, alginate oligosaccharide and/or a salt thereof (hereafter, it may be referred to as "alginate oligosaccharide (salt)"). The alginate oligosaccharide and/or a salt thereof is absorbed by the body, unlike existing salts of alginate polysaccharide or low-molecular-weight alginate, it exhibits salt-absorption inhibitory activity by a mechanism that is different from that of existing salts of alginate polysaccharide or low-molecular-weight alginate, and it also exhibits activity of protecting blood vessels. In the present invention, the term "salt" refers to sodium chloride.

A specific example of alginate oligosaccharide (salt) is an oligosaccharide having 4,5-unsaturated uronic acid at the end and comprising D-mannuronic acid and L-guluronic acid as constitutive sugars. Preferable examples of such alginate oligosaccharide (salt) include those represented by formula 1:

(formula 1)

in formula 1, R represents a hydrogen atom or metal ion, and examples of metal ions include alkali metal ions (e.g., $Na^+$ and $K^+$), alkaline earth metal ions (e.g., $Ca^{2+}$ and $Mg^{2+}$), and other metal ions (e.g., $Zn^{2+}$, $Fe^{2+}$, and $Fe^{3+}$).

Examples of salts of alginate oligosaccharide include metal salts of alginate oligosaccharide (e.g., sodium alginate oligosaccharide, potassium alginate oligosaccharide, calcium alginate oligosaccharide, and mixtures thereof).

In formula 1, R' represents D-mannuronic acid represented by formula 2 (hereafter, it may be referred to as "M") or L-guluronic acid represented by formula 3 (hereafter, it may be referred to as "G"). Alternatively, R' represents a structure in which two or more constitutive sugars comprising either or both M and G as constitutive sugars have an α- and/or β-1,4-bound structure.

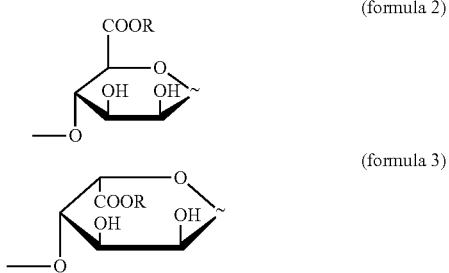

In formulae 2 and 3, R is as defined above. In formulae 1 to 3, Rs may differ from or be the same as each other.

Specific examples of R' include G, M, G-G, M-G, M-M, G-G-G, G-G-M, G-M-G, G-M-M, M-G-G, M-M-G, M-M-M, and M-G-M.

In the present invention, any compound (a single compound) or two or more compounds represented by formula 1 can be used as alginate oligosaccharide (salt).

Alginate oligosaccharide (salt) represented by formula 1 is obtained by degrading at least alginate polysaccharide, salt of alginate polysaccharide, or alginic acid ester, and preferably alginic acid and/or a salt thereof, with a polysaccharide-degrading enzyme.

Examples of alginic acid salts include metal salts of alginic acid. Examples of such "metal" include alkali metals, alkaline earth metals, and other metals exemplified with respect to R above. Specific examples of alginic acid salts include sodium alginate, potassium alginate, and mixtures thereof.

An example of a polysaccharide-degrading enzyme is an enzyme produced by a microorganism, such as alginate lyase.

An example of a microorganism that produces a polysaccharide-degrading enzyme is a *Pseudoalteromonas* microorganism, such as the *Pseudoalteromonas* sp. (*Alteromonas* sp.) strain No. 1786. The *Pseudoalteromonas* sp. strain No. 1786 was separated from horseshoe crab intestines as a result of screening of fish and shellfish intestines and the contents thereof with the use of sodium alginate as a sole carbon source. Morphological and physiological properties of such strain are as described below.

(Properties of Strain)
—Morphological Properties:
 1) Affinity for Gram's stain: negative
 2) Cellular form: *Bacillus*
 3) Colony hue: opalescence
 4) Motility: motile
 5) Presence of flagella: polar flagellum
—Physiological Properties
 1) O—F test: oxidation
 2) Oxidase test: positive
 3) Gelatin degradaion: positive
 4) DNA degradation: positive
 5) Halophilism: positive
—GC Content: 49.1 mol %

This strain was deposited with the National Institute of Bioscience and Human Technology, Agency of Industrial Science and Technology, Ministry of International Trade and Industry (currently International Patent Organism Depository, the National Institute of Advanced Industrial Science and Technology, AIST Tsukuba Central 6, 1-1-1 Higashi, Tsukuba, Ibaraki, Japan) under the Accession Number FERM BP-5201 (date of original deposit: Aug. 28, 1990). The strain was classified as the *Alteromonas* microorganism at the time of deposition; however, it is classified as the *Pseudoalteromonas* microorganism at present due to a modification of microorganism classification (J. Appl. Glycosci., 55, 81-88, 2008).

Degradation by a polysaccharide-degrading enzyme is conducted by, for example, first culturing the strain to obtain a culture product. Subsequently, alginate lyase is separated from the culture product. The separated alginate lyase is allowed to react with alginate polysaccharide and/or a salt of alginate polysaccharide, alginate polysaccharide and/or a salt of alginate polysaccharide is degraded, and alginate oligosaccharide (salt) is then generated. Thereafter, alginate oligosaccharide (salt) is separated and purified, according to need.

An example of a medium used for culture is a medium containing sodium alginate (1.00%), sodium sulfate (1.00%), potassium chloride (0.08%), magnesium sulfate (heptahydrate) (1.24%), dibasic potassium phosphate (trihydrate) (0.01%), ammonium chloride (0.10%), ammonium ferric citrate (III) (green) (0.01%), and calcium chloride (0.15%).

Culture is conducted by, for example, preculturing the lyophilized *Pseudoalteromonas* sp. strain No. 1786 twice (at 25° C. for 2 days each time) and then conducting main culture (at 25° C. for 1 day).

The thus-obtained culture product contains a culture supernatant or a microorganism in which alginate lyase has accumulated.

Subsequently, alginate lyase is separated from the culture product by a method used for protein separation and purification. Specifically, cells are removed from the culture product with the use of a ultrafilter memberane having a molecular weight cutoff of 500,000 (Romicon Inc.) to prepare a crude alginate lyase solution. Further, the alginate lyase solution is purified via, for example, salting-out, centrifugation, various chromatography techniques, or electrophoresis in adquate combination, according to need. Examples of chromatography techniques include hydrophobic, gel filtration, ion exchange, reverse phase, and affinity chromatography techniques. In order to inspect the degree of purification and the molecular weight of the purified product, SDS (lauryl sodium sulfate) polyacrylamide electrophoresis, gel filtration, or other techniques can be performed.

Subsequently, the separated alginate lyase is allowed to react with alginic acid (salt) preferably in the presence of a buffer or the like. An example of a buffer is a sodium phosphate buffer. Reaction is preferably conducted at 45° C. to 55° C. (50° C. in particular) and at a pH of 7.0 to 7.5 (7.0 in particular).

Thereafter, alginate oligosaccharide (salt) generated is separated and purified, so as to yield the number of constitutive sugars according to need. Alginate oligosaccharide (salt) can be separated and purified by, for example, gel filtration, salting-out, or various chromatography techniques. In the case of small-scale separation and purification (approximately several grams), specifically, the oligosaccharide (salt) is injected into a column filled with gel filtration carriers for oligosaccharide (salt) fractionation to elute a substance of interest with the aid of desalted water (JP Patent Publication (kokai) No. H4-169188 A (1992)). As the gel filtration carriers for oligosaccharide (salt) fractionation, those with a molecular weigh cuttoff range of 100 to 1,800 daltons are preferable, and specific examples thereof include Bio-Gel P-2 and Bio-Gel P-6DG (Bio-Rad). In the case of large-scale separation and purification (several hundred grams or more), an electrodialyzer (Microacilyzer, Asahi Kasei, Co.) is preferably used.

Treatment can also be carried out with the use of a culture product (e.g., a culture solution), cells, or treated cells (e.g., broken cells, extracted cells, or crude enzymes) instead of or in combination with purified enzymes.

In addition, the vascular protecting agent having salt-absorption inhibitory activity of the present invention may comprise another alginate oligosaccharide (salt) other than the alginate oligosaccharide (salt) mentioned above obtained via degradation with a polysaccharide-degrading enzyme. Products obtained via hydrolysis of at least one of alginic acid, alginic acid salt, and alginic acid ester with an acid or alkali can be used as such alginate oligosaccharide (salt).

Alginic acid extracted from brown algae seaweed, such as *Laminaria, Undaria pinnatifida*, or *Hizikia*, can be used.

Salts exemplified with regard to degradation by the polysaccharide-degrading enzyme can be used as alginic acid salts. Specific examples include alkali metal salts of alginic acid (e.g., sodium salt and potassium salt) and alkaline earth metal salts of alginic acid (e.g., calcium salts and magnesium salts).

Examples of alginic acid esters include alkylene polyhydric alcohol esters of alginic acid (e.g., propylene glycol ester and ethylene glycol ester) and alkyl esters (e.g., ethyl ester and methyl ester).

An example of an acid is mineral acid (e.g., phosphoric acid or hydrochloric acid). Phosphoric acid concentration is preferably 50% to 90% by weight.

An example of an alkali is sodium hydroxide.

Hydrolysis is preferably carried out at 0° C. to 60° C. (20° C. to 40° C. in particular) for 1 hour to 1 month.

The molecular weight and molecular weight distribution of alginate oligosaccharide (salt) can be controlled by regulating the acid or alkali concentration and hydrolysis conditions. The number average molecular weight (Mn) is generally 10,000 or less, preferably 3,500 or less, more preferably 2,000 or less, and most preferably 1,500 or less.

Subsequently, alginate oligosaccharide (salt) is separated from the hydrolysis mixture as a degradation product. Specifically, water is added to the hydrolysis mixture to dissolve the degradation product. Subsequently, this aqueous solution is separated, a hydrophilic organic solvent is added to the aqueous solution to precipitate the degradation product, and the precipitated degradation product is fractionated. Thus, alginate oligosaccharide (salt) can be separated.

In such a case, the amount of water added is preferably 0.2 to 100 times greater than that of the hydrolysis mixture (the weight-volume ratio). When the amount of water is too small, the aqueous solution may become highly viscous and occasionally become hard to handle. When the amount of water is too large, however, reprecipitation (deposition) in the hydrophilic organic solvent may become difficult.

Examples of hydrophilic organic solvents include water-soluble organic solvents, such as methanol, ethanol, and isopropanol.

Alginate oligosaccharide (salt) used for the vascular protecting agent having salt-absorption inhibitory activity of the present invention is obtained in the manner described above. Dehydration products of the alginate oligosaccharide (salt) via lyophilization, spray drying, hot air drying, or other means can be used for the vascular protecting agent having salt-absorption inhibitory activity of the present invention.

The vascular protecting agent having salt-absorption inhibitory activity of the present invention can be used as a pharmaceutical product for the purpose of reducing adverse effects imposed by excessive salt stress in humans and protecting blood vessels from damages caused by various factors. The vascular protecting agent of the present invention can also be used for animals other than humans for similar purposes. The vascular protecting agent having salt-absorption inhibitory activity of the present invention is administered orally. The form of administration is not limited. Examples include powders, tablets, capsules, powdered drugs, granules, fine grains, syrup, emulsions, suspensions, and aqueous solutions. The form of administration can be adequately determined regardless of the age and health condition of a person who ingests the agent. Such agents for oral administration may contain carriers, diluents, and excipients that are generally used in the field of pharmaceutical preparations. For example, lactose and magnesium stearate can be used as carriers or excipients for tablets. The vascular protecting agent having salt-absorption inhibitory activity of the present invention can be incorporated into various types of agents, regardless of the form of administration. In such a case, the amount of the vascular protecting agent having salt-absorption inhibitory activity of the present invention incorporated is preferably 0.01% to 20% by weight, and particularly preferably 0.1% to 10% by weight, relative to the whole amount.

It is preferable that, for example, an adult with a body weight of 60 kg ingest the vascular protecting agent having salt-absorption inhibitory activity of the present invention in such a manner that the amount of alginate oligosaccharide (salt) as an active ingredient ingested is preferably 0.1 g to 20 g, and more preferably 0.5 g to 5 g per day in one or several separate instances over two or more consecutive days. Content of alginate oligosaccharide (salt) as an active ingredient of the vascular protecting agent having salt-absorption inhibitory activity of the present invention may be determined using the aforementioned amount of ingestion as an indication and taking the number of instances of ingestion or dosage per day into consideration.

The vascular protecting agent having salt-absorption inhibitory activity of the present invention is absorbed by the body through the intestinal tract after it was orally ingested, and it then exhibits the effects thereof.

Also, the vascular protecting agent having salt-absorption inhibitory activity of the present invention may be administered parenterally to a living organism in the form of a parenteral agent. Examples of routes of parenteral administration include subcutaneous administration and intravenous administration, and subcutaneous administration in the form of a subcutaneous agent is preferable. When the vascular protecting agent of the present invention is parenterally administered, the agent exibits its effects after being absorbed by the body. In order to exert effects, in the case of parenteral administration, the amount administered per day can be smaller than that in the case of oral administration. Equivalent effects can be attained with 1/50 to 1/150 of the amount necessary for oral administration. In addition, equivalent effects can be attained within a shorter duration of administration than oral administration. When the vascular protecting agent having salt-absorption inhibitory activity of the present invention is used in the form of a parenteral agent, the agent may contain a carrier, diluent, or excipient that is commonly used in the field of pharmaceutical preparations. Examples thereof include an extender, a binder, a disintegrator, a pH modifier, and a solubilizer. Examples of dosage forms of parenteral agents include, but are not limited to, a liquid, an emulsion, a suspension, and an injection preparation.

When the vascular protecting agent having salt-absorption inhibitory activity of the present invention is administered orally, it is preferable that, for example, an adult with a body weight of 60 kg ingest the vascular protecting agent in such a manner that the amount of alginate oligosaccharide (salt) as an active ingredient ingested is preferably 0.01 mg to 10,000 mg, and more preferably 0.05 mg to 5,000 mg per day in one or several separate instances over two or more consecutive days. The content of alginate oligosaccharide (salt) as an active ingredient of the vascular protecting agent having salt-absorption inhibitory activity of the present invention may be determined using the aforementioned amount of ingestion as an indication and taking the number of instances of ingestion or dosage per day into consideration.

In the present invention, the term "salt-absorption inhibitory activity" refers to activity of inhibiting absorption of salt by the body, and this activity mainly inhibits absorption through the digestive tract. Blood vessel protection is protection of blood vessels from various vascular diseases or protection of blood vessels during treatment of vascular diseases. The term "protection" refers to enhancement of resistivity to various types of stress imposed on blood vessels, including those caused by salt. For example, stress on blood vessels caused by the elevated blood pressure is reduced, cardiac blood vessels are protected to reduce stress on the heart caused by the elevated blood pressure, and blood vessels and the heart are protected to suppress deterioration in cardiac functions. In addition, blood vessels of the kidney can be protected and glomerulosclerosis can be suppressed in the kidney. Further, blood vessels of the kidney can be protected to increase the creatine clearance in the kidney, thereby suppressing the deterioration of renal functions. By protecting blood vessels with the use of the vascular protecting agent of the present invention, glomerular damage can be suppressed, and normal functions of the glomeruli can be maintained. Also, the progression of kidney failure can be delayed, and the initiation of dialysis treatment can be delayed.

In addition, the vascular protecting agent having salt-absorption inhibitory activity of the present invention may be mixed with a food or beverage product and used in the form of a composition for a food or beverage product. Also, the agent may be mixed with animal feed, such as pet food. Examples of food or beverage products include health food or beverage products, food or beverage products for specified health use, food or beverage products with nutrient function claims, and health supplementary food or beverage products. The term "food or beverage product for specified health use" used herein refers to a food product to be ingested for a specified health maintenance purpose in dietary habit in cases in which such ingestion can lead to achievement of an intended health maintenance purpose. Such food or beverage products may be provided with indications that the products are intended for protection of blood vessels or strengthening or reinforcement of blood vessels, for example.

EXAMPLES

The present invention is described in detail with reference to the following examples, although the present invention is not limited thereto.

Example 1

Preparation of Alginate Oligosaccharide (Salt)

Preparation Example 1

The lyophilized *Pseudoalteromonas* sp. strain No. 1786 was cultured twice in a medium having the composition described below; preculture was conducted at 25° C. for 2 days and the main culture was then conducted at 25° C. for 1 day. As a result, an alginate lyase culture solution having enzyme activity of 0.90 units per ml of culture solution was produced. Cells were removed from the culture solution using an ultrafilter memberane having a molecular weight cutoff of 500,000 (Romicon Inc.) to prepare a crude alginate lyase solution.

Composition of the culture medium: 1.00% sodium alginate, 1.00% sodium sulfate, 0.08% potassium chloride, 1.24% magnesium sulfate (heptahydrate), 0.01% dibasic potassium phosphate (trihydrate), 0.10% ammonium chloride, 0.01% ammonium ferric citrate (III)(green), and 0.15% calcium chloride Sodium alginate (10.0 kg) was dissolved in 90 liters of desalted water, the crude alginate lyase solution (50,000 U) obtained above was added thereto, and the reaction was allowed to proceed at 40° C. for 6 hours while the mixture was agitated. After the reaction solution was deproteinized and desalted, the resultant was lyophilized to obtain 4.2 kg of sodium alginate oligosaccharide powder.

The structure of the sodium alginate oligosaccharide (Preparation Example 1; a compound represented by any of formulae 1 to 3 wherein R represents sodium) was analyzed in the following manner. The degree of polymerization was determined via mass spectrometry (using a liquid chromatograph-mass spectrometer manufactured by JASCO International Co., Ltd.) and NMR analysis (using an NMR apparatus manufactured by JEOL Ltd.).

Sodium alginate oligosaccharide (Preparation Example 1) was subjected to high-performance liquid chromatography (HPLC) using the IEC DEAE-825 column (manufactured by Shodex) via gradient elution with NaCl (0.25 M), and the resultant was fractionated using a fraction collector. The elution pattern is shown in FIG. 1.

Fractions exhibiting absorbance at 230 nm (P1 to P8) were recovered and desalted with the use of an electrodialyzer (Microacilyzer, Asahi Kasei, Co.).

When such fractions were subjected to chromatography again under the same conditions, oligosaccharides having properties as shown in Table 1 were obtained. As a result of mass spectrometry of such oligosaccharides, peaks at m/z values as shown in Table 1 were detected, and the degrees of polymerization thereof were deduced based on such m/z values.

As a result of NMR analysis, further, sodium alginate oligosaccharide at each peak value (P1 to P8) was found to have a structure shown below in which constitutive sugars were α- or β-1,4-bound to each other. D represents 4,5-unsaturated uronic acid.

P1: D-G
P2: D-M
P3: D-G-G
P4: D-M-G
P5: D-M-M
P6: D-G-G-G
P7: D-G-G-M1D-G-M-G
 : D-G-M-M, D-M-G-G
 : D-M-M-G, D-M-M-M
P8: D-M-G-M

Preparation Examples 2 and 3

Potassium alginate oligosaccharide (Preparation Example 2) and a mixture of potassium alginate oligosaccharide with sodium alginate oligosaccharide (Preparation Example 3) were obtained in the same manner as described above, except that potassium alginate and a mixture of potassium alginate with sodium alginate were used, respectively, instead of sodium alginate.

Preparation Example 4

Sodium alginate oligosaccharide (Preparation Example 1) and potassium alginate oligosaccharide (Preparation Example 2) obtained above were treated with the use of the aforementioned electrodialyzer with various water-soluble calcium salts, including calcium acetate, to obtain calcium alginate oligosaccharides.

Preparation Example 5

The alginate lyase solution was added to an aqueous solution containing 13% sodium alginate by weight, and the reaction was allowed to proceed at 40° C. for 40 hours while the mixture was agitated. The reaction solution was filtered through an ultrafilter memberane having a molecular weight cutoff of 30,000 to obtain sodium alginate oligosaccharide powder (Preparation Example 5).

Sodium alginate oligosaccharide obtained (Preparation Example 5) was subjected to HPLC analysis (FIG. 2) and structural analysis in the same manner as in Preparation Example 1. As a result, sodium alginate oligosaccharide at each peak value (P1 to P5) was found to have a structure shown below in which constitutive sugars were α- or β-1,4-bound to each other.

P1: D-G
P2: D-G-G
P3: D-M-G
P4: D-G-G-G
P5: D-G-G-M, D-G-M-G
: D-G-M-M, D-M-G-G
: D-M-M-G, D-M-M-M

Preparation Example 6

Propylene glycol esters of alginic acid (commercial product, 5.0 g) were dissolved in 45 ml of a solution containing 85% by weight phosphoric acid, and the resultant was allowed to stand at 40° C. for 3 days. Methanol (100 ml) was added thereto, the mixture was agitated, the resultant was allowed to stand for 2 hours, the precipitated solid was filtered, the resulting solid (a filter cake) was washed until it was neutralized, and the resultant was dried to obtain 1.3 g of a hydrolysate (yield: 26.0%).

The molecular weight of the resulting hydrolysate (Preparation Example 6) was measured, and Mn/Mw (the weight average molecular weight) was found to be 3,200/24,000.

The molecular weight was measured using a gel permeation chromatography system (high-performance GPC HLC-8120, manufactured by Tosoh Corp.). TSK-gel G5000PWXL and G3000PWXL columns (manufactured by Tosoh Corp.) were used, sodium polyacrylate was used as a reference material, and a 0.025 M phosphate buffer was used as an eluant.

Example 2

Confirmation of Absorbability

Acclimated 8-week-old male Wistar rats (4 rats, Charles River Laboratories Japan, Inc.) were forced to undergo oral administration of alginate oligosaccharide powder in an amount of 5 g/kg through a feeding tube. Blood sampling was carried out by the tail-cutting method before administration and 0.5, 1, 2, 4, and 6 hours after administration, and blood serum samples were prepared by a conventional technique. The separated blood serum samples were diluted with distilled water at 1:1, and the resultants were centrifuged using Ultrafree-MC Filter Units (10,000 NMWL, non-sterile, Millipore) at 5,000 g for 6 hours. The filtrate was recovered, and the dUMGM-4Na content, which is the source of the main peak of alginate oligosaccharide, was measured via HPLC using a DEAE column (gradient from 0 to 0.25 M NaCl).

Figure 2:
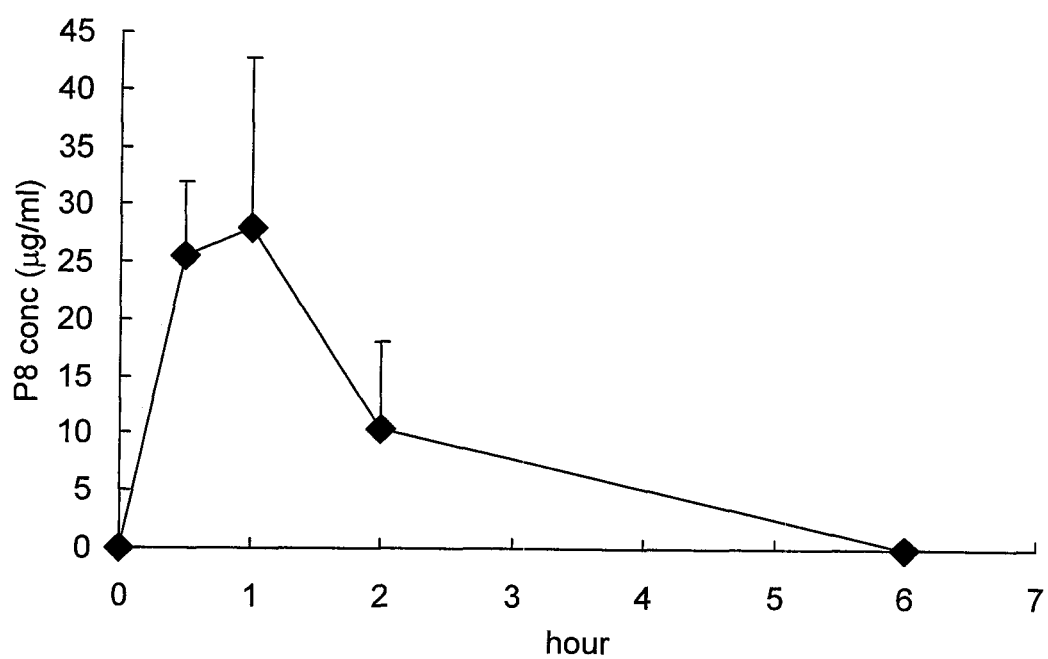
FIG. 2 shows the absorbability of alginate oligosaccharide by the body.

As a result, it was found that the dUMGM-4Na concentration in the blood serum reached the maximal level 1 hour after administration, following which it decreased, and the concentration fell below the detection limit 6 hours after administration (FIG. 2). This suggests that some of the alginate oligosaccharide that had been orally administered would be absorbed by the body and then metabolized and eliminated from the blood 6 hours later.

Acclimated 8-week-old male SHR rats (3 rats) were subjected to free ingestion of dUMGM-4Na as a main component of alginate oligosaccharide in the form of a 5% feed mixture. Urine sampling was then conducted up to 24 hours later with the elapse of time. Urine samples were diluted with distilled water at 1:1, and the resultants were centrifuged using Ultrafree-MC Filter Units (10,000 NMWL, non-sterile, Millipore) at 5,000 g for 6 hours. The filtrate was recovered, and the dUMGM-4Na content was measured via HPLC using a DEAE column (gradient from 0 to 0.25 M NaCl). The amount of dUMGM-4Na ingested was determined based on the amount of the feed mixture ingested.

As a result, 1.12% of the orally ingested dUMGM-4Na was considered to have been excreted into the urine 24 hours after ingestion.

TABLE 1

| Time of urine sampling (hours) | Amount of ingestion (mg) | Amount of dUMGM-4Na (mg) | Recovery (%) |
| --- | --- | --- | --- |
| 4 | 300 | 0.39 | 0.13 |
| 6 | 550 | 0.72 | 0.13 |
| 12 | 700 | 2.10 | 0.30 |
| 24 | 1000 | 5.60 | 0.56 |

Example 3

Studies in Case where High Salt Stress is Applied to the Cardiovascular System and Alginate Oligosaccharide is Orally Administered Acclimated 4-week-old male Dahl salt-sensitive rats (24 rats, Dahl S, SRL) were divided into 4 groups each consisting of 8 rats (n=8), and these groups of rats were raised while being fed with feed containing 0.3% salt (the low-salt-stress group), feed containing 4% salt (the control group), feed containing 4% salt and 4% alginate oligosaccharide (the low-dose group), and feed containing 4% salt and 8% alginate oligosaccharide (the high-dose group), respectively, for 7 weeks (all test feeds were manufactured by Oriental Yeast Co., Ltd., and rats were allowed to freely ingest feed and drink water). The systolic blood pressure was measured by the tail-cuff method every week. Urine sampling was conducted with the use of metabolic cages over a period of 24 hours every 2 weeks. After the test period, rats were subjected to exsanguination through the ventral aorta under nembutal anesthesia and euthanized. The heart, the kidney, and the pars thoracica aortae were extracted.

Figure 3:
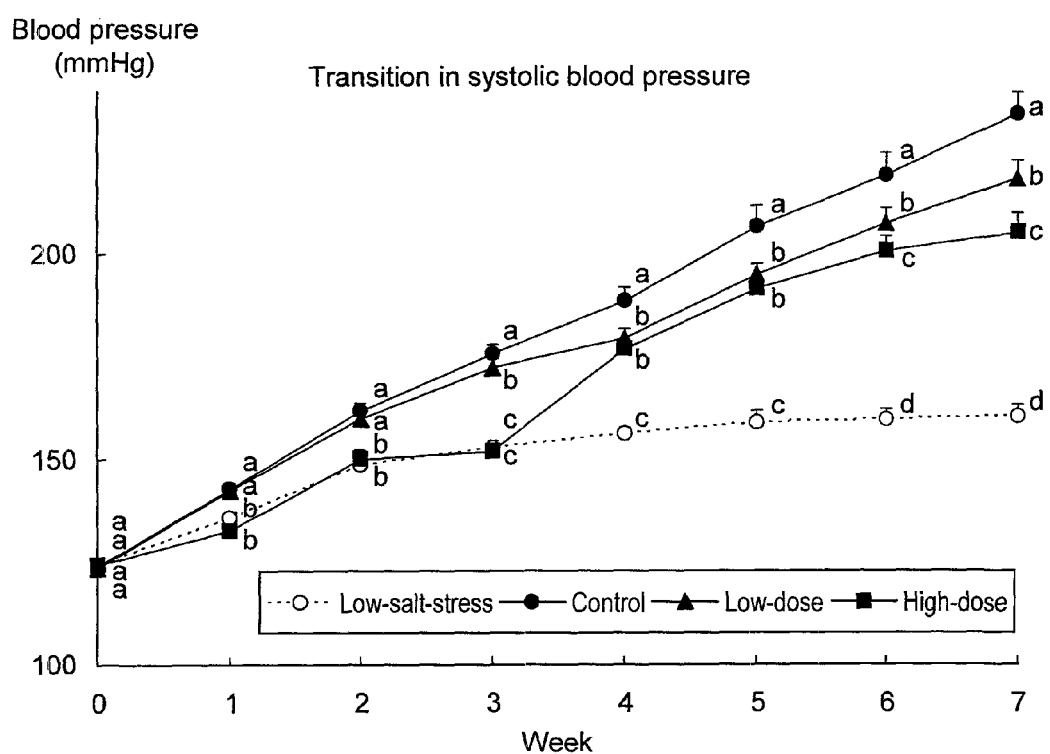
FIG. 3 shows the effects of alginate oligosaccharide on the influence of salt stress on blood pressure.

Evaluation of Protective Activity Against Stress Applied to Cardiovascular System As a result of the test, the systolic blood pressure levels were found to be significantly elevated in the three groups that had been exposed to salt stress compared with the low-salt-stress group (FIG. 3). In the groups to which alginate oligosaccharide had been administered, elevation in the systolic blood pressure levels was suppressed in accordance with the dose. Since Dahl S rats exhibit elevated blood pressure levels upon salt stress application, the apparent influence of salt contained in the feed was observed, and the possibility that alginate oligosaccharide had reduced such influence was suggested.

Evaluation of Influence of Alginate Oligosaccharide on Sodium Metabolism

Figure 4:
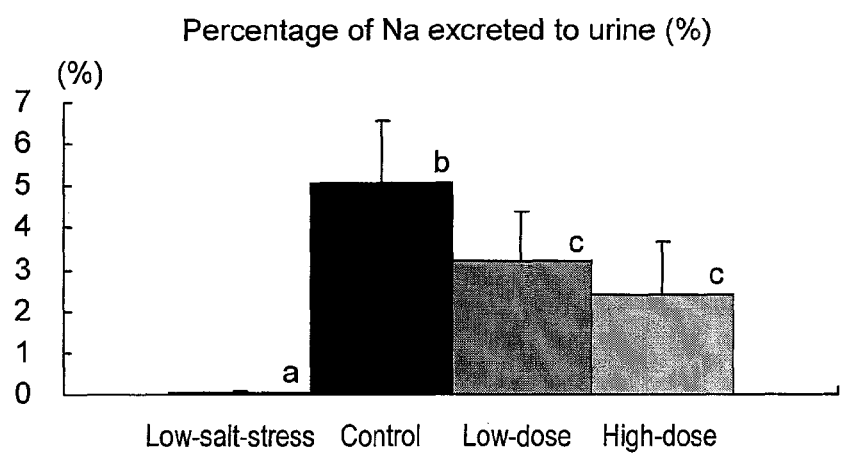
FIG. 4 shows the influence of alginate oligosaccharide on sodium metabolism.

Sodium excretion into the urine was evaluated in order to determine whether or not activity of alginate oligosaccharide for blood vessel protection observed in the form of suppression of blood pressure elevation was caused by suppression of salt absorption or acceleration of excretion. As a result, the groups to which alginate oligosaccharide had been administered (the low-dose group and the high-dose group) were found to exhibit significantly lowered sodium excretion levels into the urine compared with the control group (FIG. 4). Since sodium excretion into the urine was suppressed in the groups to which alginate oligosaccharide had been administered to a greater degree than in the control group, specifically, the observed activity was considered to result from inhibition of absorption instead of acceleration of salt excretion.

Evaluation of Influence of Alginate Oligosaccharide on Vascular Weight/Body Weight Ratio As a result of induction of severe high blood pressure by application of high-salt stress to the vascular system, the pars thoracica aortae weight/body weight ratio, which is significantly influenced by blood pressure level, of the control group was significantly higher than that of the low-salt-stress group, and thickening of the blood vessel wall was induced. Since the groups to which alginate oligosaccharide had been administered exhibited a significantly lower pars thoracica aortae weight/body weight ratio than the control group, the possibility that the blood vessels were protected from stress caused by severe high blood pressure was suggested.

Figure 5:
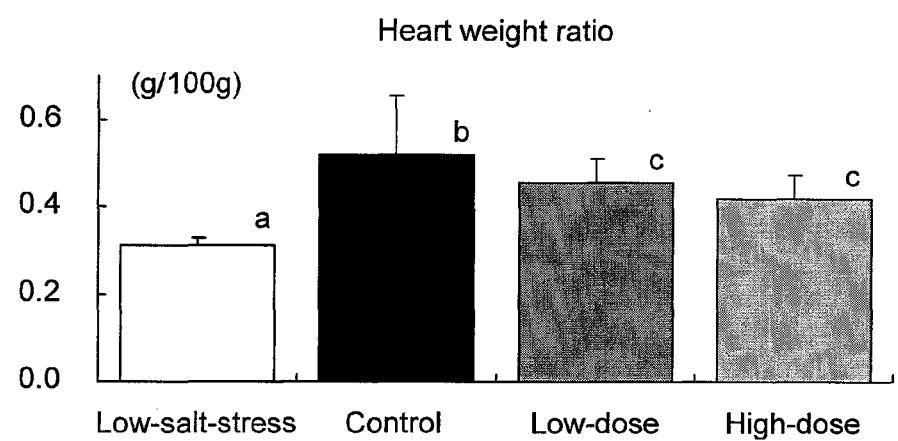
FIG. 5 shows the influence of alginate oligosaccharide on the heart weight/body weight ratio.

Evaluation of Influence of Alginate Oligosaccharide on Heart Weight/Body Weight Ratio As a result of stress application to the vascular system by application of high-salt stress, the heart weight/body weight ratio of the control group was significantly higher than that of the low-salt-stress group, and cardiac hypertrophy was induced. Since the groups to which alginate oligosaccharide had been administered exhibited a significantly lower heart weight/body weight ratio than the control group (FIG. 5), the possibility that the heart was protected from stress caused by severe high blood pressure was suggested.

Figure 6:
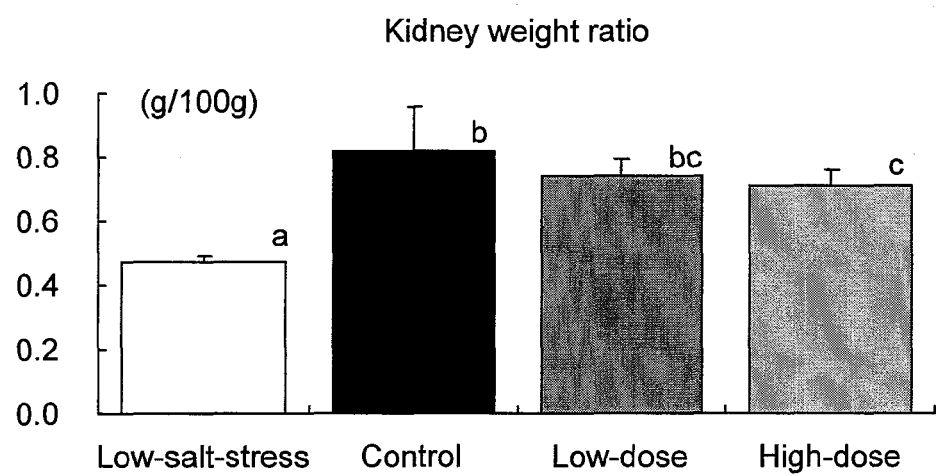
FIG. 6 shows the influence of alginate oligosaccharide on the kidney weight/body weight ratio.

Evaluation of Influence of Alginate Oligosaccharide on Kidney Weight/Body Weight Ratio As a result of stress application to the vascular system by application of high-salt stress, the kidney weight/body weight ratio of the control group was significantly higher than that of the low-salt-stress group, and renal hypertrophy was induced. The groups to which alginate oligosaccharide had been administered exhibited a lower value than the control group in accordance with dose, and the high-dose group exhibited a significantly lower value compared with the control group (FIG. 6). These results suggest that the kidney, which is an organ comprising many capillary blood vessels and is susceptible to elevated blood pressure, may have been protected from stress caused by severe high blood pressure.

Figure 7:
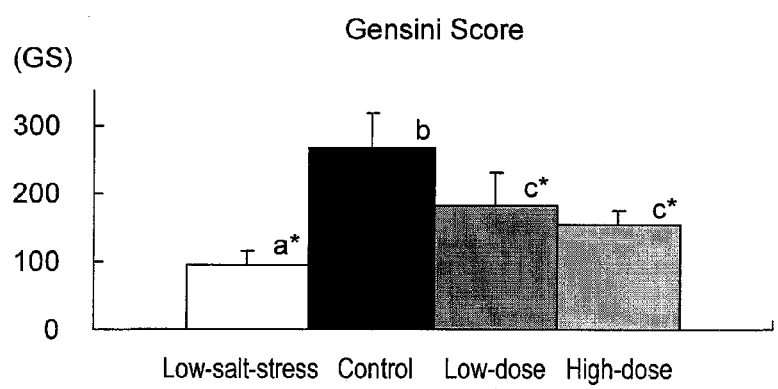
FIG. 7 shows the influence of alginate oligosaccharide on the degree of glomerular hardening (Part 1).
Figure 8:
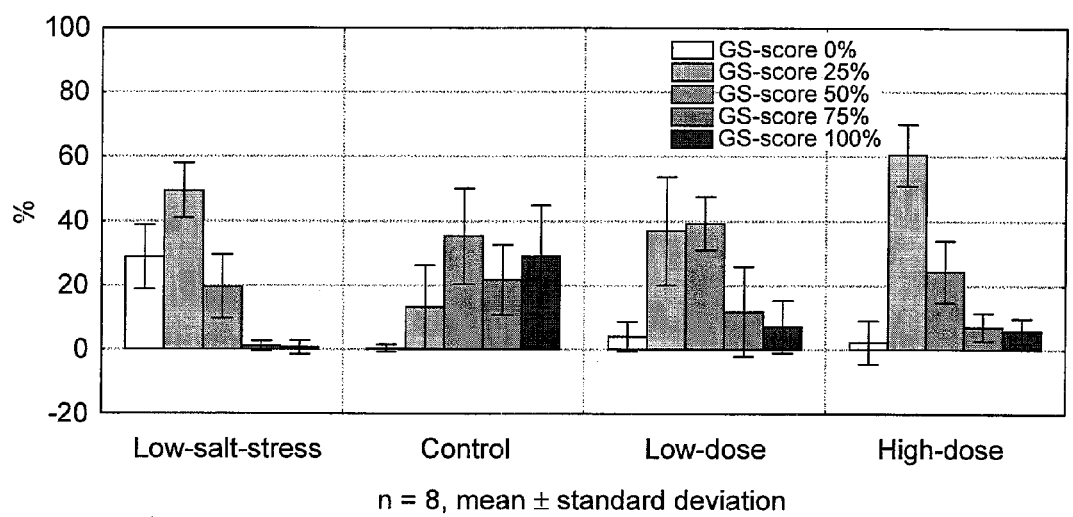
FIG. 8 shows the influence of alginate oligosaccharide on the degree of glomerular hardening (Part 2).

Evaluation of Influence of Alginate Oligosaccharide on Degree of Glomerular Hardening The degree of glomerular hardening was evaluated as part of the evaluation of glomerular functions. As a result of induction of severe high blood pressure by application of high-salt stress to the vascular system, the degree of glomerular hardening of the control group was significantly higher than that of the low-salt-stress group, and such glomerular hardening was considered to have advanced (FIG. 7). Since the groups to which alginate oligosaccharide had been administered exhibited a lower value than the control group in accordance with dose and a decreased percentage of serious cases among all cases, glomerular hardening was considered to have been suppressed (FIG. 8). These results suggest that alginate oligosaccharide exhibited activity of protecting the glomeruli composed of many capillary blood vessels from stress caused by high blood pressure.

Evaluation of Influence of Alginate Oligosaccharide on Creatinine Clearance

Figure 9:
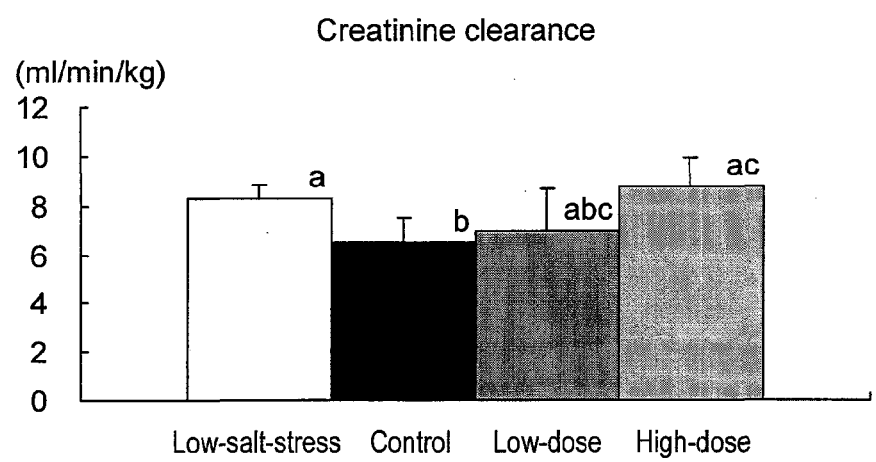
FIG. 9 shows the influence of alginate oligosaccharide on creatinine clearance.

Creatinine clearance was evaluated as part of the evaluation of renal functions. Since severe high blood pressure induced by high-salt stress applied stress to the kidney, the creatinine clearance of the control group was significantly lower than that of the low-salt-stress group. The groups to which alginate oligosaccharide had been administered exhibited the improvement compared with the control group in a dose-dependent manner and the high-dose group exhibited a significantly lowered value (FIG. 9). This suggests the possibility that blood vessels may have been protected from stress caused by severe high blood pressure in the kidney comprising many capillary blood vessels, and a reduction in renal functions may have been consequently suppressed.

Evaluation of Influence of Alginate Oligosaccharide on Urinary Protein

Figure 10:
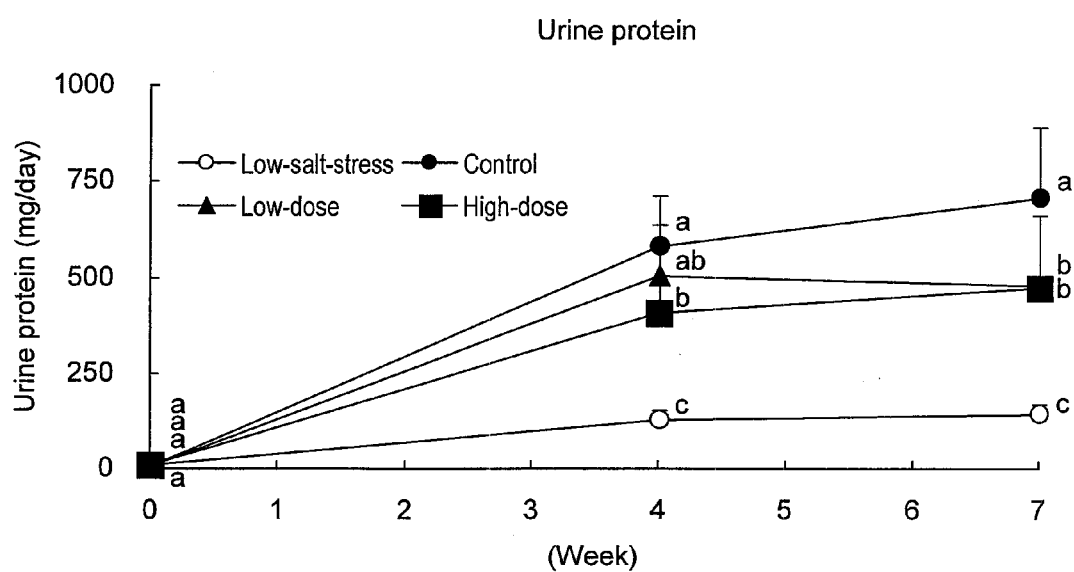
FIG. 10 shows the influence of alginate oligosaccharide on urinary protein.

Urinary protein was evaluated as part of the evaluation of glomerular functions. Since severe high blood pressure induced by high-salt stress applied stress to the kidney, elevation in urinary protein levels was observed in the control group with the elapse of time, and the resulting value was significantly higher than that for the low-salt-stress group. The groups to which alginate oligosaccharide had been administered exhibited a significantly lower value than the control group (FIG. 10). This suggests the possibility that blood vessels may have been protected from stress caused by severe high blood pressure in the kidney comprising many capillary blood vessels, and a reduction in renal functions may have been consequently suppressed.

Example 4

When High Salt Stress is Applied to the Cardiovascular System and Alginate Oligosaccharide is Subcutaneously Administered Acclimated 6-week-old male Dahl salt-sensitive rats (20 rats, Dahl S, SRL) were divided into 3 groups, and feed containing 0.3% salt (the low-salt-stress group), feed containing 4% salt (the control group), and subcutaneous administration of 4% salt and alginate oligosaccharide (the subcutaneous administration group) were applied to these groups of rats, respectively. All test feeds were manufactured by Oriental Yeast Co., Ltd., and rats were allowed to freely ingest feed and drink water. To the subcutaneous administration group, alginate oligosaccharide was administered with the use of a continuous osmotic minipump in an amount of 6 mg per day for 2 weeks after the initiation of the test, and administration was immediately terminated thereafter. Rats were raised for 3 weeks in total, during which the systolic blood pressure was measured by the tail-cuff method.

Figure 11:
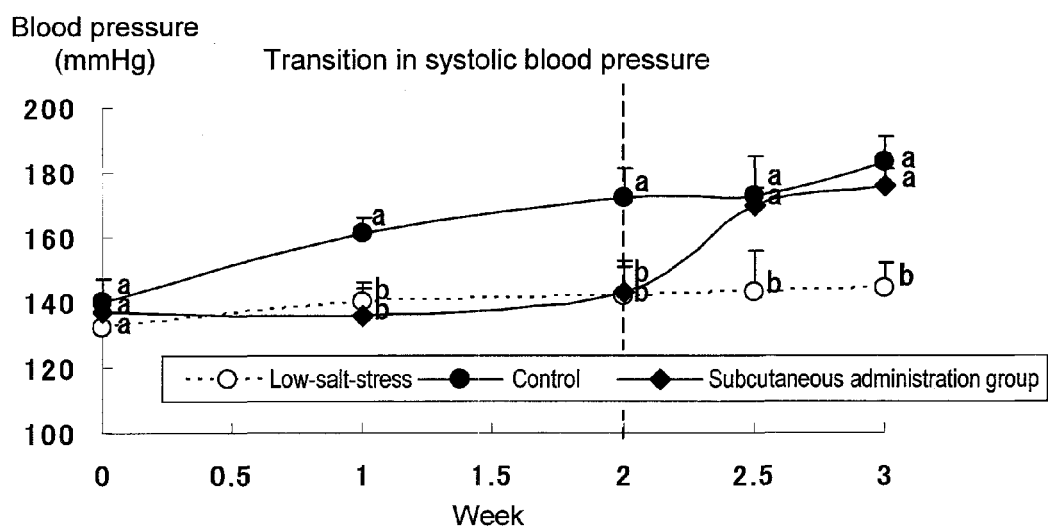
FIG. 11 shows the influence of alginate oligosaccharide on blood pressure.

The results are shown in FIG. 11. As shown in FIG. 11, the systolic blood pressure level did not change in the low-salt-stress group during the test period; however, the systolic blood pressure level was elevated in the control group with the elapse of time, and the systolic blood pressure of the control group was significantly higher than that of the low-salt-stress group. While elevation of the systolic blood pressure had not been observed in the subcutaneous administration group while alginate oligosaccharide was being administered, the systolic blood pressure was elevated immediately after termination of administration, and it reached a level equivalent to that of the control group 1 week after termination of administration.

Effects were observed via subcutaneous administration of alginate oligosaccharide. This strongly suggests that alginate oligosaccharide may exert its effects after being absorbed by the body instead of when inside the intestinal tract. Also, the amount to be ingested per day may be as small as 1/50 to 1/150 that used in the case of oral administration in order for effects to be exerted. While it took approximately 4 weeks to observe apparent effects in the case of oral administration, the effects were observed within approximately 2 weeks in the case of subcutaneous administration. This indicates that subcutaneous administration can exert stronger effects than oral administration.

Industrial Applicability

The vascular protecting agent of the present invention can be used in the form of a pharmaceutical or food or beverage product for blood vessel protection.

Accession Number

FERM BP-5201

The invention claimed is:

1. A method for suppressing thickening of the blood vessel by inhibiting salt-absorption, which comprises administering an alginate oligosaccharide and/or salt thereof to a patient in need thereof, wherein the alginate oligosaccharide and/or salt thereof of formula 1:

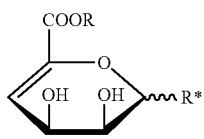
(formula 1)

wherein in formula 1,
R is a hydrogen atom or a metal ion;
R' is a structure selected from the group consisting of G; G-G; M-G; G-G-G; G-G-M; G-M-G; G-M-M; M-G-G; M-M-G; and M-M-M, wherein the linkage among D-mannuronic acid (M) and L-guluronic acid (G) is α- or β-1,4-bound.

2. The method according to claim 1, wherein the alginate oligosaccharide and/or salt thereof is obtained by treating sodium alginate with a *Pseudoalteromonas* microorganism.

3. The method according to claim 2, wherein the *Pseudoalteromonas* microorganism is the *Pseudoalteromonas* sp. strain No. 1786.

4. A method for suppressing cardiac hypertrophy by protecting a vascular, which comprises administering an alginate oligosaccharide and/or salt thereof to a patient in need thereof, wherein the alginate oligosaccharide and/or salt thereof of formula 1:

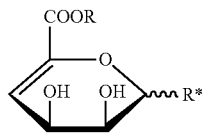
(formula 1)

wherein in formula 1,
R is a hydrogen atom or a metal ion;
R' is a structure selected from the group consisting of G; G-G; M-G; G-G-G; G-G-M; G-M-G; G-M-M; M-G-G; M-M-G; and M-M-M, wherein the linkage among D-mannuronic acid (M) and L-guluronic acid (G) is α- or β-1,4-bound.

5. A method for suppressing renal hypertrophy and/or glomerular hardening by protecting a vascular, which comprises administering an alginate oligosaccharide and/or salt thereof to a patient in need thereof, wherein the alginate oligosaccharide and/or salt thereof of formula 1:

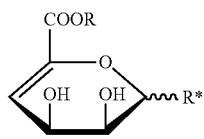
(formula 1)

wherein in formula 1,
R is a hydrogen atom or a metal ion;
R' is a structure selected from the group consisting of G; G-G; M-G; G-G-G; G-G-M; G-M-G; G-M-M; M-G-G; M-M-G; and M-M-M, wherein the linkage among D-mannuronic acid (M) and L-guluronic acid (G) is α- or β-1,4-bound.

6. The method according to claim 1, wherein the alginate oligosaccharide and/or salt thereof is subcutaneously administered.

7. The method according to claim 4, wherein the alginate oligosaccharide and/or salt thereof is subcutaneously administered.

8. The method according to claim 5, wherein the alginate oligosaccharide and/or salt thereof is subcutaneously administered.

9. The method according to claim 4, wherein the alginate oligosaccharide and/or salt thereof is obtained by treating sodium alginate with a *Pseudoalteromonas* microorganism.

10. The method according to claim 9, wherein the *Pseudoalteromonas* microorganism is the *Pseudoalteromonas* sp. strain No. 1786.

11. The method according to claim 5, wherein the alginate oligosaccharide and/or salt thereof is obtained by treating sodium alginate with a *Pseudoalteromonas* microorganism.

12. The method according to claim 11, wherein the *Pseudoalteromonas* microorganism is the *Pseudoalteromonas* sp. strain No. 1786.

* * * * *